United States Patent [19]

Pettit et al.

[11] Patent Number: 5,076,973
[45] Date of Patent: Dec. 31, 1991

[54] SYNTHESIS OF DOLASTATIN 3

[75] Inventors: George R. Pettit, Paradise Valley, Ariz.; Cedric W. Holzapfel, Johannesburg, South Africa

[73] Assignee: Arizona Board of Regents, Tempe, Ariz.

[21] Appl. No.: 261,311

[22] Filed: Oct. 24, 1988

[51] Int. Cl.$^5$ .......................... C07K 3/04; C07K 5/12; C07K 7/64
[52] U.S. Cl. .................. 530/333; 530/317; 530/330
[58] Field of Search .................. 514/9, 326, 11; 530/333, 331, 330, 317

[56] References Cited

U.S. PATENT DOCUMENTS

| | | | |
|---|---|---|---|
| 4,291,007 | 9/1987 | Dutta et al. | 530/331 |
| 4,882,420 | 11/1989 | Thaisrivongs | 530/330 |
| 4,886,813 | 12/1989 | Nakamura et al. | 514/326 |
| 4,898,977 | 2/1990 | Herold et al. | 564/191 |

OTHER PUBLICATIONS

Stewart et al. (1984) *Solid Phase Peptide Synthesis* (2d, ed) Laboratory Techniques in Solid Phase Peptide Synthesis, pp. 53–124.

*Primary Examiner*—Lester L. Lee
*Assistant Examiner*—Avis M. Davenport
*Attorney, Agent, or Firm*—Richard R. Mybeck

[57] ABSTRACT

Synthesis of dolastatin 3 is accomplished by one amino acid unit addition from L-Pro-OMe employing diethyl phosphorocyanidate-triethylamine for peptide bond formation and N-Boc protection (trifluoroacetic acid cleavage). Thereafter Boc-L-Leu-L-(gln)Thz-(gly)Thz-L-Val-L-Pro-OMe was obtained, successively crystallized from ethanol-diethyl ether, converted to the OPfp active ester, Boc cleavage and cyclization in dioxane containing t-butanol and 4-pyrrolidinopyridine to yield synthetic (-)-dolastatin 3.

21 Claims, No Drawings

SYNTHESIS OF DOLASTATIN 3

INTRODUCTION

The present invention relates generally to chemical synthesis and more particularly to the synthesis of the substance denominated "dolastatin 3". Ever since dolastatin 3 was extracted by G. R. Pettit from Indian Ocean sea hare Dolabella, isolated, and found to possess cell growth inhibitory properties, that synthesis of the substance has been a major dilemma. The present invention represents the ultimate resolution of that dilemma. Partial funding of this project was obtained from P.H.S Grant CA-16049-08-11 and NSF Grants CHE-8409644 and CHE-8620177.

BACKGROUND OF THE INVENTION

Dolastatin 3 was first isolated and elucidated by Dr. George R. Pettit and found to possess potent cell growth inhibitory powers (See U.S. Pat. No. 4,414,205 for detailed history). However, the vast number of Dolabella needed to provide sufficient Dolastatin 3 to meet the projected public need effectively prevented this remarkable substance from ever being considered for commercial production. Further, the inability to tightly replicate the natural substance from lot to lot because of the entrainment of even slight amounts of unidentifiable impurities in the extracted product created problems which prevented the natural substance from meeting the strict uniformity requirements set forth by the Food and Drug and Cosmetic Administration and corresponding regulatory agencies in other countries as a condition precedent to the approval of the introduction of a new drug product to the market place.

Thus, the need to develop an economically viable and truly replicable synthetic procedure for producing substantially pure Dolastatin 3 in large quantities is the principal object of the present invention.

BRIEF SUMMARY OF THE INVENTION

Synthesis of dolastatin 3 is accomplished by one L-amino acid unit additions from L-Pro-OMe employing diethyl phosphorocyanidate (DEPC)-triethylamine for peptide bond formation and N-Boc-protection (trifluoroacetic acid cleavage). The thiazole amino acid components used herein were prepared as described by Schmidt et al (*Synthesis*, 1987, 233-236; Schmidt et al, *Synthesis*, 1986, 992-998; Kelly et al, *J. Org. Chem.*, 1986, 51, 4590-4594; Houssin et al, *J. Org. Chem.*, 1985, 50, 2787-2788; and Holzapfel et al, *J. Org. Chem.*, 1985, 50, 2323-2327). By these means, Boc-L-Leu--L-(gln)Thz-(gly)Thz-L-Val-L-Pro-OMe, mp 125°-126° from ethyl acetate-hexane, $[\alpha]D^{25.8} -74.9$ (c=3.73, CHCl$_3$) was obtained in 71% overall yield. After successive hydrolysis [1N NaOH, dioxane 3N HCl→mp 168°-170° from ethanol-diethyl ether, $[\alpha]D^{22} -37.7$ (c=1.64, CH$_3$OH), conversion (DCCI, DME, pentafluorophenol) to the OPfp active ester, Boc cleavage, and cyclization in dioxane containing 4% t-butanol and 4-pyrrolidinopyridine (at 95° C., 76% yield), synthetic (-)-dolastatin 3, a colorless amorphous solid from ethanol-ethyl acetate, mp 170°-173°, $[\alpha]D^{25} -53.3$ (c=0.94 in CHCl$_3$), $^1$H- and $^{13}$C-NMR was realized in 41% overall yield.

Accordingly, a principal object of the present invention is to provide an effective and commercially viable process for synthesizing dolastatin 3.

A further object of the present invention is to provide a process for synthesizing dolastatin 3 utilizing one L-amino acid unit additions from L-Pro-OMe employing diethyl phosphorocyanidate (DEPC)-triethylamine for peptide bond formation and N-Boc protection (trifluoroacetic acid cleavage).

These and still further objects as shall hereinafter appear are fulfilled by the present inventor in a remarkably unexpected fashion as shall hereinafter be discerned from a careful consideration of the following detailed description of exemplary embodiments thereof.

DESCRIPTION OF PREFERRED EMBODIMENTS

Because of the P388 lymphocytic leukemia (PS) cell growth inhibition displayed by dolastatin 3, an unusual cyclic pentapeptide containing two thiazole amino acid units, the elucidation of its complete structure and the synthetic replication has been the focus of intensive interest. In 1979, about 1 mg of amorphous dolastatin 3 was isolated from 100 kg. (wet wt.) of the Indian Ocean sea hare *Dolabella auricularia*. Based on interpretation of results from the best instrumental techniques then available, and presuming an all L-configuration, a structure was tentatively assigned which was later eliminated. Further work eliminated the chiral isomers, the reverse order of bonding, and a modified amino acid. When the remaining dolastatin 3 decomposed in storage, reisolation was required which provided only 1.8 mg. [$1.8 \times 10^{-6}$% yield, mp 155°-159°, $[\alpha]D^{29} -48.5$ (c=0.01, CH$_3$CH)] of dolastatin 3. Using the latest advances in high field (400 and 500 MHz) $^1$H-NMR and other special techniques, the structure for dolastatin 3 was ultimately and unequivocally determined from which the total synthesis of dolastatin 3 was developed as will hereinafter be described in detail.

Acid hydrolysis (6N HCl, 110° C., 24-72 h) of natural (-)-dolastatin 3 and examination of the hydrolysate (as N-trifluoroacetyl-n-butyl ester derivatives) by chiral gas chromatographic (fused silica column coated with "Chirasil-Val") analysis indicated that the Val, Pro and Leu units all belonged to the L-configurational series. The configuration of (gln)-Thz was solved by the synthetic routes described below. Results of a two-dimensional NMR study using $^1$H, $^1$H-COSY and H-[H]-NOE difference experiments (See: Table 1) supported the selection of sequence modification described for dolastatin 3. The structure designated herein for dolastatin 3 has been unequivocally confirmed as will be demonstrated. Further, the chirality of the (gln)Thz unit is clearly established by synthesis.

In accordance with the present invention, dolastatin 3 was synthesized by one L-amino acid unit additions from L-Pro-OMe employing diethyl phosphorocyanidate (DEPC)-triethylamine for peptide bond formation and N-Boc-protection (trifluoroacetic acid cleavage). The thiazole amino acid components were prepared as described above. By this means, Boc-L-Leu-L-(gln)Thz-(gly)Thz-L-Val-L-Pro-OMe [mp 125°-126° from ethyl acetatehexane, $[\alpha]D^{25.8} -74.9$ (c=3.73, CHCl$_3$)] was obtained in 71% overall yield. After successive hydrolysis [1N NaOH, dioxane 3N HCl→mp 168°-170° from ethanol-diethyl ether, $[\alpha]D^{22} -37.7$ (c=1.64, CH$_3$CH)], conversion (DCCI, DME, pentafluorophenol) to the OPfp active ester, Boc cleavage, and cyclization (in dioxane containing 4% t-butanol and 4-pyrrolidinopyridine at 95°, 76% yield), synthetic (-)-dolastatin 3, a colorless amorphous solid from ethanol-ethyl acetate, mp 170°-173°, $[\alpha]D^{25}-53.3$ (c=0.94 in $CHCl_3$), $^1H$- and $^{13}C$-NMR as shown below in Tables I and II, was realized in 41% overall yield.

The synthetic (-)-dolastatin 3 produced by the present invention, as shown in Table I below, was identical with the natural product. Comparison $^1H$-NMR (400 MHz) spectra observed in methylene chloride-$d^2$ were superimposable as were SP-HRSIMS[14] spectra, and thin layer chromatographic comparisons (on silica gel, normal and reverse phase) in four different (e.g., 90:10:0.8 methylene chloride-methanol-water) solvent systems. Both specimens of dolastatin 3, namely, the natural and the synthetic, inhibited growth of the PS leukemia to the same extent ($ED_{50}=16$ vs. 0.17 ug/ml), and displayed an identical tendency to undergo decomposition in solution, especially in chloroform. The difficulties experienced in uncovering appropriate experimental conditions for cyclizing the linear pentapeptide precursor of (-)-dolastatin 3 combined with its sensitivity and biological activity suggests that its overall conformational preferences are very important. Other isomers of dolastatin 3 so far examined are quite stable but are inactive against the PS system.

TABLE I

Dolastatin 3 assignments in deuteriochloroform solution relative to tetramethylsilane for $^1H,^1H$-connectivity by NOE experiments

| Position Irradiated | $^1H$ Chemical Shift, ppm | Connectivity by $^1H$-$(^1H)$-NOE Difference | % NOE |
|---|---|---|---|
| 25 | 8.32 | N25H, C24H | 0.8 |
| | | N25H, C24cH | 0.8 |
| 24 | 4.75 | C24H, C24bH | 1.1 |
| | | C24H, C24cH | 1.1 |
| | | C24H, C21H | 2.7 |
| 18 | 3.97 | C18H, N16H | 1.3 |
| | | C18H, C19H | 0.8 |
| 16 | 6.01 | N16H, C18H | 4.1 |
| | | N16H, C15H | 3.3 |
| 13 | 7.85 | N13H, C15H | 0.8 |
| | | N13H, N16H | 0.8 |
| | | N13H, C12H | 1.0 |
| | | N13H, C12aH | 1.1 |
| 12 | 5.54 | C12H, C12aH | 2.3 |
| | | C12H, C12bH | 1.3 |
| 12d | 5.42 | N12d, C12bH | 0.5 |
| | 6.25 | N12d, C12bH | 0.7 |
| 5 | 8.76 | N5H, C4H | 1.2 |
| | | N5H, C4H | 1.7 |
| 4 | 5.23 | C4H, N5H | 0.8 |

The detailed structural elucidation and synthesis of dolastatin 3 as described herein will enable the full biological, chemical, and commercial potential of this important marine organism biosynthetic product to be realized. The structure is as follows:

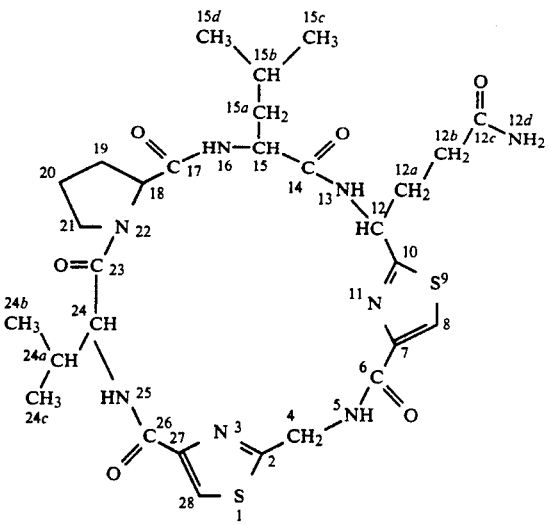

In one practice of the present invention, triethylamine and diethyl phosphorocyanidate ("DEPC") are added to S-proline methyl ester and N-t-Boc-L-valine in 1,2-dimethoxyethane at 0° C. After holding for one hour at 0° C., the mixture is allowed to warm to room temperature ("RT") over 4 hours and diluted with ethyl acetate. The diluted mixture is then washed with 5% HCl followed by sodium hydrogen carbonate followed with saturated brine. The solvent is then removed by vacuum (in vacuo) to yield N-t-Boc-L-Val-L-Pro-OMe as a colorless syrup.

The colorless syrup is then stirred into a solution of dry dichloromethane at 0C. and trifluoroacetic acid is added thereto. After one hour at 0° C. and one hour at RT, the mixture is diluted with dry carbon tetrachloride and the solvents are removed therefrom in vacuo leaving a colorless syrup residue which is dried under vacuum for 12 hours leaving the dipeptide trifluoroacetate.

The trifluoroacetate from above and N-t-Boc-(gly)Thz are placed in dry dimethoxyethane and the resultant solution is cooled to 0° C. To the cooled solution, triethylamine and DEPC are added and the solution is maintained at 0° C. for one hour and thereafter warmed to RT over 4 hours. The solution is then diluted with ethyl acetate and washed with 5% HCl followed by a wash with sodium hydrogen carbonate and, thereafter, saturated brine.

The organic phase is then dried with anhydrous sodium sulfate and the solvent is removed therefrom in vacuo. The residue is N-t-Boc-(gly)Thz-L-Val-L-Pro-OMe as a colorless syrup.

The residue is placed in dry dichloromethane at 0° C. and trifluoroacetic acid is added thereto and the mixture is held at 0° C. for one hour. Thereafter, the mixture is warmed to room temperature for one hour and diluted with carbon tetrachloride. The solvents are then removed in vacuo leaving the tripeptide trifluoroacetate as a colorless syrup which is dried under vacuum for 24 hours and dissolved in dry dimethylformamide to form a solution.

N-t-Boc-L-(gln)Thz is added to the solution and cooled to 0° C. Triethylamine and DEPC are then added to the cooled solution which is held at 0° C. for one hour and raised to room temperature for six hours. The solvents are removed from the room temperature solution in vacuo leaving, as a residue, the protected tetrapeptide, N-t-Boc-L-(gln)Thz-(gly)Thz-L-Val-L-Pro-OMe.

The protected tetrapeptide is then dissolved in trifluoroacetic acid at 0° C., warmed to room temperature, and diluted with carbon tetrachloride. The solvents are then removed in vacuo leaving the tetrapeptide trifluoroacetate as a residue which is then dried under vacuum for 24 hours and dissolved in dimethylformamide to form a solution.

N-t-Boc-L-Leu is then added to the solution which is cooled to 0° C. Triethylamine and DEPC are then added to the cooled solution which is retained at 0° C. for one hour and warmed to room temperature for 4 hours. The solvents are then removed therefrom in vacuo and the residue is purified by chromatography on a silica column in 7% methanol and ethylacetate to provide the protected pentapeptide as an amorphous white powder having a melting point of 125°-126° C. The residue is N-t-Boc-L-Leu-L-(gln)Thz-(gly)Thz-L-Val-L-Pro-OMe.

The protected pentapeptide is placed in dioxane and water, treated with 1N NaOH at room temperature for 3 hours, and diluted with diethyl ether. Next, the aqueous phase is collected and the pH thereof was adjusted to 2 with ice cold 2N HCl and extracted with chloroform. The several extracts are combined and dried with anhydrous sodium sulfate. The solvents are then removed in vacuo leaving the N-Boc-pentapeptide which is then precipitated from ethanol with diethyl ether.

The precipitate is then placed in dry dimethoxyethane and dimethylformamide, treated with pentafluorophenol and N,N'-dicyclohexyl- carbodiimide at -20° C. in a nitrogen atmosphere and then warmed to and held at room temperature for 12 hours. The warmed solution is then filtered to remove dicyclohexylurea therefrom. The solvents are then removed in vacuo and the pentapeptide pentafluorophenyl ester is collected and treated with trifluoroacetic acid at room temperature.

The reaction mixture is diluted with carbon tetrachloride and the solvents removed therefrom in vacuo. The resulting residue, the pentapeptide trifluoroacetate ester, is dried under vacuum and dissolved is dioxane to produce a solution which is added to a stirred solution of 4-pyrrolidinopyridine in t-butanol and dioxane at 95° C. After two and one-half hours, the solution is cooled and then filtered through celite. The solvents are then removed from the residue in vacuo leaving as an amorphous white powder, Cyclo-[L-Val-L-Pro-L-Leu-L-(gln)Thz-(gly)Thz], herein denominated "dolastatin 3".

To further aid in the understanding of the present invention, and not by way of limitation, the following examples as presented.

EXAMPLE I

The following experimental criteria were employed to synthesize Dolastatin 3. The Boc-L-Leu, L-Pro-OMeHCl and Boc-L-Val were obtained from Sigma Chemical Co., the dimethoxyethane and dioxane were distilled from sodium; and the dimethylformamide was distilled from calcium hydride. Thin layer chromatography (TLC) was accomplished with Whatman silica gel KSF (250µ) plates. Column chromatography procedures were accomplished with 70-230 mesh silica (E. Merck, Darmstadt) or Sephadex ® LH-20 (Pharmacia Fine Chemicals, AB, Uppsala, Sweden). Nuclear magnetic resonance spectra were recorded on a Varian VXS-200 or Bruker WP-500 instruments using tetramethylsilane as internal standard. Infrared spectra were recorded in chloroform solutions. Mass spectra were determined with a Varian MAT-212/55-188 mass spectrometer.

EXAMPLE II

N-t-Boc-S-Val-S-Pro-OMe was prepared as follows. To a stirred solution of S-proline methyl ester (4 g, 24.15 mmol) and N-t-Boc-L-Valine (5.29 g, 24.15 mmol) in 1,2-dimethoxyethane at 0° C. were added triethylamine (7.07ml, 50.72 mmol) and diethyl phosphorocyanidate (4.03 ml, 26.56 mmol). After 1 hour at 0° C. and 4 hours at room temperature the reaction mixture was diluted with ethyl acetate (250 ml) and washed successively with 5% hydrochloric acid (1 x 50 ml), aqueous sodium hydrogen-carbonate (1×50 ml) and with saturated brine (1×50 ml). Removal of the solvent in vacuo and chromatography of the residue furnished the protected dipeptide N-t-Boc-L-Val-L-Pro-OMe as a colorless syrup (7.29 g, 92%), $[\alpha]D^{25}$ −70.0° (c 4.0, chloroform); MS (EI) accurate mass m/z 328.1984 (M+, calc. 328.1998 for $C_{16}H_{28}N_2O_5$); $\gamma_{max}$3420, 1740, 1700 and 1640 cm$^{-1}$; $^1$H-NMR (CDCl$_3$)δ0.91 (3H, d, J =6.6 Hz, CH$_3$CH), 1.00(3H, d, J =6.6 Hz, CH$_3$CH), 1.40 (9H, s, (CH$_3$)$_3$C), 1.85-2.30 (4H, m), 2.00 (1H, m (CH$_3$)$_2$CH), 3.55-3.80 (2H, m, N—CH$_2$), 3.69 (3H, s, OCH$_3$), 4.25 (1H, dd, J=9.2 and 6.3 Hz, NCHCON), 4.50 (1H, m, NCHCOOCH$_3$), 5.18 (1H, d, J =9.2 Hz, NHCO); $^{13}$C-NMR (CDCl$_3$)δ17.33 (q), 19.24 (q), 24.96 (t), 28.31 (q)[1], 29.00 (t), 31.31 (d), 47.08 (t), 52.12 (q), 56.77 (d), 58.74 (d), 79.41 (s), 155.84 (s), 171.15 (s), 172.44 (s).

EXAMPLE III

N-t-Boc-(gly)Thz-L-Val-L-Pro-OMe was prepared from the N-t-Boc-L-Val-L-Pro-OMe produced in Example II as follows. To a stirred solution of N-t-Boc-L-Val-L-Pro-OMe (3.93 g, 11.96 mmol) in dry dichloromethane (20 ml) at 0° C., trifluoro- acetic acid (20 ml) was added dropwise. After 1 hour at 0° C. and 1 hour at room temperature, the reaction mixture was diluted with dry carbon tetrachloride (100 ml) and the solvents removed in vacuo. The residue, a colorless syrup, was dried under vacuum for 12 hours. Without further purification this material, the dipeptide trifluoroacetate, and N-t-Boc-(gly)Thz (3.09 g, 11.96 mmol) were dissolved in dry dimethoxyethane (9 ml ). The solution was cooled to 0° C. and triethylamine (3.66 ml, 26.31 mmol) and diethyl phosphorocyanidate (2.0 ml, 13.16 mmol) were added dropwise. After 1 hour at 0° C. the mixture was allowed to warm to room temperature. After 4 hours the mixture was diluted with ethyl acetate (100 ml) and successively washed with 5% hydrochloric acid (1×50 ml), aqueous sodium hydrogencarbonate (1×50 ml) and saturated brine (1×50 ml). The organic phase was dried (anhydrous sodium sulphate) and the solvent removed in vacuo. Chromatography of the residue on a column of silica gel (250 g) in 3:7 hexaneethyl acetate furnished the protected tripeptide N-t-Boc-(gly)Thz-L-Val-L-Pro-OMe. (5.09 g, 91%) as a colorless syrup; $[\alpha]D^{25}$−39.8° (c2.44, chloroform), MS (EI) exact mass m/z 468.2029 (M+, calc. 468.2043 for $C_{21}H_{32}N_4O_6S$); $\gamma_{max}$3440, 3380, 1740, 1720 and 1640 cm$^{-1}$; $^1$H-NMR (CDCl$_3$) δ0.98 (3H,d,J =6.6 Hz,CH$_3$CH), 1.06 (3H, d, J =6.6 Hz, CH$_3$CH), 1.43 (9H, s, (CH$_3$)$_3$C, 1.88-2.30 (4H, m), 2.00 (1H, m, (CH$_3$)$_2$CH), 3.69 (1H, m) and 3 85 (1H, m, CH$_2$NCO), 3.70 (3H, s, OCH$_3$), 4.51 (1H, m, NCHCOOCH$_3$), 4.52 (2H, m, CH$_2$NHCO), 4.72 (1H, dd, J =9.2 and 7.1 Hz, CH-NHCO), 5.40 (1H, brt, NH-Boc), 7.90 (1H, d, J=9.2 Hz, CHNHCO), 7.95 (1H, s, thiazole proton); $^{13}$C-NMR (CDCl$_3$) δ17.93 (q), 19.24 (q), 24.99 (t), 28.29 (q)$^2$, 29.05 (t), 31.57 (d), 42.24, (t), 47.30 (t), 52.18 (q), 55.55 (d), 58.87 (d), 80.10 (s), 123.72 (d), 149.33 (s), 155.52 (s), 160.82 (s), 169.0 (s), 170.49 (s), 172.41 (s).

EXAMPLE IV

N-t-Boc-L-(gln)Thz-(gly)Thz-L-Val-L-Pro-OMe was prepared by adding 4 ml of Trifluoroacetic acid dropwise to a stirred solution of N-t-Boc-(gly)Thz-R-Val-Pro-OMe (500 mg, 1.07 mmol) prepared according to Example III in dry dichloromethane at 0° C. After 1 hour at 0° C. and 1 hour at room temperature the reaction mixture was diluted with carbon tetrachloride (20 ml) and the solvents removed in vacuo to furnish the tripeptide trifluoroacetate as a colorless syrup. The product was dried under vacuum for 24 hours and dissolved in dry dimethylformamide (3 ml). N-t-Boc-L-(gln)Thz (350 mg, 1.07 mmol) was added to the solution. The mixture was cooled to 0° C. and triethylamine (0.33 ml, 2.35 mmol and diethyl phosphorocyanidate (0.18 ml, 1.18 mmol) was added dropwise over a period of 0.5 hour. After 1 hour at 0° C. and 6 hours at room temperature the solvents were removed in vacuo. The residue was chromatographed on Sephadex LH-20 in 2:1 chloroformmethanol to furnish the protected tetrapeptide, N-t-Boc-L-(gln)Thz-(gly)Thz-L- Val-L-Pro-OMe (674 mg, 93%), m.p. 129°-130° C. (from ethyl acetate-hexane) $[\alpha]D^{26}$−70.6° (c=1.3, chlorofrm), m/z 679 (M+),$\gamma_{max}$ 3400, 1740, 1665, 1640 cm$^{-1}$, $^1$H-NMR (CDCl$_3$)δ1.01 (3H, d, J=6.8Hz, CH$_3$CH), 1.08 (3H, d, J=6.8 Hz, CH$_3$CH), 1.41 (9H, s, (CH$_3$)$_3$C), 1.80-2.40 (9H, m), 3.68 (1H, m) and 3.79 (1H, m) (CH$_2$NCO), 3.72 (3H, s, OCH$_3$), 4.55 (1H, m, NCHCOOCH$_3$), 4.76 (1H, dd, J=9.3 and 7.1 Hz, CHNH), 4.77 (1H, dd, J=16.5 and 5.2 Hz) and 4.95 (1H, dd, J=16.5 and 6.1 Hz) (—CH$_2$NHCO), 4.94 (1H, m, CH$_2$CHNH), 5.55(1h, brs) and 6.36 (1H, brs, CONH$_2$), 6.26 (1H, d, J =8.1 Hz, NHBoc), 7.88 (1H, d, J =9.5 Hz, CHNH), 8.03 (1H, s) and 8.04 (1H, s,) (thiazole protons), 8.33 (1H, dd, J =6.1 and 5.2 Hz, CH$_2$NH), $^{13}$C-NMR (CDCl$_3$)δ18.02 (q), 19.22 (q), 24.88 (t), 28.30 (q)*, 29.08(t), 30.18 (t), 31.75 (t), 31.89 (d), 40.67 (t), 47.48 (t), 52.31 (q), 52.50 (d), 55.42 (d), 58.70 (d), 80.17 (s), 123.75 (d), 124.23 (d), 148.97 (s), 149.05 (s), 155.80 (s), 160.53 (s), 161.01 (s), 166.82 (s), 170.76 (s), 172.48 (s), 173.21 (s), 174.89 (s), Anal. Calcd. for C$_{29}$H$_{41}$N$_7$O$_8$S$_2$: C, 51.23, H, 6.09; N, 14:44. Found: C, 51.34; H, 6.18; N, 14.30.

EXAMPLE V

N-t-Boc-L-Leu-L-(gln)Thz-(gly)Thz-L-Val-L-Pro-OMe was prepared by dissolving N-t-Boc-L-(gln)Thz-L-Val-L-Pro-OMe (531 mg, 0.78 mmol), prepared according to Example IV, in trifluoroacetic acid (4 ml) at 0° C. After 15 min. at 0° C. the mixture was allowed to warm to room temperature. After 45 min. at this temperature the reaction mixture was diluted with carbon tetrachloride (40 ml) and the solvents removed in vacuo. The residue, the tetrapeptide trifluoroacetate as a colorless glass, was dried under vacuum for 24 hours and dissolved in dimethylformamide (8 ml). N-t-Boc-L-Leu (217 mg, 0.94 mmol) was added and the solution cooled to 0° C. To this solution triethylamine (0.26 ml, 1.88 mmol) and diethyl phosphorocyanidate (0.14 ml, 0.94 mmol) were added dropwise. After 1 hour at 0° C. and 4 hours at room temperature the solvents were removed in vacuo. The residue was chromatographed on Sephadex LH-20 in 2:1 chloroform-methanol. The main fraction was further purified by chromatography on a silica column (50 g) in 7% methanol in ethylacetate to furnish the protected pentapeptide, N-t-Boc-L-Leu-L-(gln)Thz-(gly)Thz-L-Val-L-Pro-OMe (533 mg, 86%) as an amorphous white powder. It had m.p. 125°-126° C. (from ethyl acetate-hexane), $[\alpha]S^{26}$−75.0° (c 3.7, chloroform), m/z 792 (M+), $\gamma_{max}$ 3400, 1740, 1660, 1640 cm$^{-1}$,$^1$H-NMR (CDCl$_3$)δ0.80 (6H, d, J =5.4 Hz, (CH$_2$CH), 0.98 (3H, d, J=6.8 Hz, CH$_3$CH), 1.06 (3H, d, J=6.6 Hz, CH$_3$CH), 1.36 (9H, s, (CH$_3$)$_3$C), 1.53 (2H, m), 1.80-2.40 (4H, m) 2.00 (1H, m, (CH$_3$)$_2$CH), 2.14 (1H, m, (CH$_3$)$_2$CH-), 2.20 (2H, m), 2.30 (2H, m), 3.68 (1H, m) and 3.89 (1H, m, CH$_2$NCO), 3.69 (3H, s, OCH$_3$), 4.22 (1H, m, CHNHCO), 4.55 (1H, m, NCHCOOCH$_3$), 4.78 (1H, dd, J=9.3 and 7.7 Hz, CH-CHNH), 4.87 (2H, d, J=5.7 Hz, CH$_2$NHCO), 5.21 (1H, m, CH$_2$CHNH), 5.31 (1H, d, J =7.65 Hz, NHBoc), 5.82 (1H, brs) and 6.60 (1H, brs, COHH$_2$), 7.90 (1H, d, J =9.3 Hz, CH-NH), 8.01 (1H, s) and 8.03 (1H, s) (thiazole protons), 8.11 (1H, d, J =7.9Hz, CHNHCO), 8.43 (1H, brs, J =5.7 Hz, CH$_2$-NH), $^{13}$C-NMR(CDCl$_3$)δ18.08 (q), 19.18 (q), 21.90 (q), 22.79 (q), 24.63 (d), 24.92 (t), 28.30(q)*, 29.12 (t), 30.21 (t), 31.68 (t), 31.74 (d), 40.82 (t), 41.78 (t), 47.54 (t), 51.00(d), 52.27 (q), 52.51 (d), 55.53 (d), 58.99 (d), 80.10 (s), 123.90 (d), 124.34 (d),148.92 (s)*, 155.72 (s), 160.65 (s), 161.12 (s), 167.34 (s), 170.78 (s), 172.28 (s), 172.28 (s), 172.57 (s), 173.47 (s), 175.00 (s). Anal. Calc. for C$_{35}$H$_{52}$N$_8$O$_9$S$_2$: C, 53.00; H, 6.62; N, 14.13; S, 8.09. Found: C, 53.08; H, 6.74; N, 14.27; S, 8.21.

EXAMPLE VI

Cyclo-[L-Val-L-Pro-L-Leu-L-(gln)Thz-gly- (Thz)], dolastatin 3, was prepared from the N-Boc pentapeptide methyl ester produced according to Example V (250 mg, 0.315 mmol) in dioxane (1.5ml) and water (1.5 ml) and treating the solution with 1N sodium hydroxide (0.315 ml) at room temperature for 3 hours. The reaction mixture was then diluted with diethyl ether (5 ml). The aqueous phase was collected, acidified to pH =2 with ice cold 3N hydrochloric acid and extracted with chloroform (3 ×8 ml). The combined extracts were dried (anhydrous sodium sulphate) and the solvent removed in vacuo to furnish the N-Boc pentapeptide (230 mg, 94%). After precipitation from ethanol with diethyl ether, it had $]\alpha]D^{22}$−37.7 (c 1.64, methanol). This compound (200 mg, 0.256 mmol) in dry dimethoxyethane (3.0 ml) and dry dimethyl- formamide (1 ml) was treated with pentafluoro- phenol (47.2 mg, 0.256 mmol) and N,N'-dicyclo-hexylcarbodiimide (52.8 mg, 0.256 mmol) at −20° C. under nitrogen. The mixture was allowed to warm to room temperature. After 12 hours the mixture was filtered to remove dicyclohexylurea. The solvents were removed in vacuo and the residue chromatographed on Sephadex LH-20 in chloroform to furnish the pentafluorophenyl ester (210 mg, 87%) as a colorless oil with R$_f$=0.42 (7% methanol in ethyl acetate).

The pentafluorophenyl ester (114 mg) was then treated with trifluoroacetic acid (6 ml) for 0.5 hours at room temperature. Dilution of the reaction mixture with carbon tetrachloride (20 ml) and removal of the solvents in vacuo furnished the pentapeptide trifluoroacetate ester as a colorless glass-like material. After drying under vacuum for 2 hours, the material was dissolved in dioxane. This solution was added by motor driven syringe over a period of 1 hour into a vigorously stirred solution of 4-pyrrolidinopyridine (17.7 mg, 0.120 mmol) in t-butanol (11 ml) and dioxane (225 ml) at 95° C. After 2.5 hours at 95° C., the mixture was cooled, filtered through celite, and the solvents were removed therefrom in vacuo. The residue was successively chromatographed on Sephadex LH-20 in chloroform and on silica in 7% methanol in chloroform to furnish the cyclic peptide, Cyclo-[L-Val-L-Pro-L-Leu-L-(gln)Thz-(gly)(Thz)], dolastatin 3 (60 mg, 76%) as an amorphous white powder. After precipitation from 1:1 ethanol-ethyl acetate with hexane it had m.p. 187°–188° C., $[\alpha]_D^{25} -53.3°$ (c 0.94, chloroform), MS(EI) m/z 660 (M+);MS (SP-SIMS) (glycerol), accurate mass m/z 661.2576 ([M+H]+, calc. 661.2591 for $C_{29}H_{41}N_8O_6S_2$; $\gamma_{max}$ 3427, 3379, 3330, 3090, 3020, 1670, 1629, 1544, 1501, 1494, 1445, 1065 cm$^{-1}$, $^1$H-HNMR (CDCl$_3$)δ0.90 (3H, d, J =6.6 Hz, H-15d), 0.95 (3H, d, J =6.6 Hz, H-15c), 1.04 (3H, d, J =6.7Hz, H-24c), 1.15 (3H, d, J =6.8 Hz, H-24b), 1.53 (1H, m, H-15b), 1.94 (2H, m, H-20), 2.05 (1H, m, H-24a), 2.13 (2H, m, H-12a), 2.24 (2H, m, H-19), 2.33 (2H, m H-15a), 2.53 (2H, m, H-12b), 3.70 (1H, m, H-21), 3.85 (2H, m, H-21, H-15), 3.97 (1H, t, J =7.9 Hz, H-18), 4.65 (1H, dd, J =18.0 and 2.0 Hz, H-4), 4.75 (1H, dd, J =9.0 and 7.0 Hz, H-24), 5.24 (1H, dd, J =18.0 and 7.2, H-4), 5.29 (1H, brs, H-12d), 5.53 (1H, ddd, J =10.9, 9.1, and 4.5 Hz, H-12), 6.02 (1H, d, J =6.6 Hz, H-16), 6.19 (1H, brs, H-12d), 7.83 (1H, d, J =9.0, H-13), 8.05 (1H, s, H-28), 8.07 (1H, s, H-8), 8.30 (1H, d, J =9.4 Hz, H-25) and 8.73 (1H, dd, J =6.9 and 2.0 Hz, H-5); $^{13}$C-NMR (CDCl$_3$)δ18.55 (C-24c), 19.53 (C-24b), 21.18 (C-15d), 23.30 (C-15C), 25.43 (C-15b), 25.45 (C-15a), 28.41 (C-19), 29.62 (C-12a), 31.88 (C-24a), 33.27 (C-12b), 37.71 (C-20), 40.97 (C-4), 48.26 (C-21), 48.61 (C-12), 54.97 (C-15), 55.62 (C-24), 62.61 (C-18), 123.71 (C-28), 124.26 (C-8), 148.30 (C-2), 149.00 (C-10), 160.30 (C-27), 160.80 (C-7), 165.77 (C-12C), 169.4 (C-17), 170.92 (C-23), 171.09 (C-26), 172.00 (C-14), 174.30 (C-6). Anal. Calc. for $C_{29}H_{40}N_8O_6S_2$: C, 52.70; H, 6.11; N,16.96; S, 9.70. Found: C, 52.82; H, 6.30; N, 16.80; S, 9.55.

EXAMPLE VII

The following NMR results were obtained for dolastatin 3 with a Bruker WP-500 instrument using a deuteriochloroform solution and tetramethyl-silane as extensive 2D-NMR experiments such as HETCOR: $^{13}$C-NMR$^8$δ18.55 (C-24c), 19.53 (C-24b), 21.18 (C-15d), 23.30 (C-15c), 25.43 (C-15b), 25.45 (C-15a), 28.41 (C-19), 29.62 (C-12a), 31.88 (C-24a), 33.27 (12b), 37.71 (C-20), 40.97 (C-4) 48.26 (C-21), 48.61 (C-12), 54.97 (C-15), 55.62 (C-24), 62.61 (C-18), 123.71 (C-28), 124.26 (C-8), 148.30 (C-2), 149.00 (C-10), 160.30 (C-27), 160.80 (C-7), 165.77

(C-12c), 169.4 (C-17), 170.92 (C-23), 171.09 (C-26), 172.00 (C-14), 174.30 (C-6); $^1$H-NMR (500 MHz)δ0.90 (3H, d, J=6.6, H-15d), 0.95 (3H, d, J=6.6, H-15c), 1.04 (3H, d, J=6.7, H-24c), 1.15 (3H, d, J=6.8, H-24b), 1.53 (1H, m, H-15b), 1.94 (2H, m, H-20), 2.05 (1H, m, H-24a), 2.13 (2H, m, H-12a), 2.24 (2H, m, H-19), 2.33 (2H, m, H-15a), 2.53 (2H, m, H-12b), 3.70 (1H, m, H-21), 3.85 (2H, m, H-21, H-15), 3.97 (1H, dd, J=7.9, H-18), 4.65 (1H, dd, J=18.0 and 2.0, H-4), 4.75 (1H, dd, J=9.0 and 7.0, H-24), 5.24 (1H, dd, J=18.0 and 7.2, H-4), 5.29 (1H, brs, H-12d), 5.53 (1H, ddd, J=10.9, 9.1, 4.5 H-12), 6.02 (1H, d, J=6.6, H-16), 6.19 (1H, brs, H-12d), 7.83 (1H, d, J=9.0, H-13), 8.05 (1H, s, H-28), 8.07 (1H, s, H-8), 8.30 (1H, d, J=9.4, H-25), and 8.73 (1H, dd, J=6.9 and 2.0, H-5).

EXAMPLE VIII

Dolastatin 3 was subjected to HR SP-SIMS analysis and the following results were obtained: Anal. Calcd. for $C_{29}H_{41}N_8O_6S_2$ (M+H): 661.2591. Found (natural): 661.2600 and Found (synthetic): 661.2576.

It was also determined that the coupling of the individual amino acids can be achieved using other methods such as N-hydroxysuccinimide/DCC although the yields were consistently better using diethyl phosphorocyanidate which also did not effect racemisation. Furthermore, the final cyclisation can also be effected using the 2,4,5-trichlorophenyl ester of the pentapeptide, but the yield was considerably lower (ca. 15%) and the product produced thereby was almost impossible to purify. An alternate synthesis of dolastatin 3 can also be obtained from the sequence R-(gln)Thz- gly(Thz)-R-Val-R-Pro-R-Leu, but cyclisation was only achievable with pentafluorophenyl ester. The preferred method of cyclization herein described is capable of yielding dolastatin 3 from any potential pentapeptide precursors.

From the foregoing, it becomes apparent that new and useful procedures have been herein described and illustrated which fulfill all of the aforestated objectives in a remarkably unexpected fashion. It is of course understood that such modifications, alterations and adaptations as may readily occur to an artisan having the ordinary skills to which this invention pertains are intended within the spirit of the present invention which is limited only by the scope of the claims appended hereto.

We claim:

1. A process for synthesizing a peptide having the structure cyclo comprising the steps of adding triethylamine and diethyl phosphorocyanidate to S-proline methyl ester and N-t-Boc-L-valine in 1,2-dimethoxyethane at 0° C. to form a dipeptide; holding said depeptide at 0° C. for one hour; allowing said dipeptide to warm to room temperature over a period of 4 hours; diluting the warmed depeptide with ethyl acetate to form a diluted mixture; washing said diluted mixture first with 5% HCl; then with sodium hydrogen carbonate and finally with saturated brine and removing the solvent therefrom in vacuo to provide N-t-Boc-L-Val-L-Pro-OMe as a colorless syrup; stirring said colorless syrup into a solution of dry dichloromethane at 0° C.; adding trifluoroacetic acid to said syrup mixture and holding said syrup mixture at 0° C. for one hour; warming said cold syrup-mixture to room temperature; holding said syrup-mixture at room temperature for one hour; diluting said warmed syrup mixture with dry carbon tetrachloride; removing the solvents from said diluted syrup mixture in vacuo to provide a colorless syrup residue; drying said colorless syrup residue under vacuum for twelve hours to provide a dipeptide trifluoroacetate; mixing said dipeptide trifluoroacetate and N-t-Boc-(gly)Thz in dry dimethoxyethane to form a solution; cooling said solution to 0° C.; adding triethylamine and DEPC to said cooled solution; holding said cooled solution 0° C. for one hour; warming said cooled solution to room temperature over four hours to for a warmed solution; diluting said warmed solution with ethyl acetate; washing said diluted warmed solution with 5% HCl and sodium hydrogen carbonate; further washing the washed diluted warmed solution with saturated brine; drying said further washed warmed solution with sodium sulfate; removing the solvent from said solution in vacuo to provide a residue of N-t-Boc- (gly)Thz-L-Val-L-Pro-OMe as a colorless syrup; placing said residue of N-t-Boc-(gly)Thz-L-Val-L-Pro-OMe in dry dichloromethane at 0° C.; adding trifluoroacetic acid to said residue and said dry dichloromethane to form a mixture; holding said mixture at 0° C. for one hour; warming said last formed mixture to room temperature for one hour; diluting said room temperature mixture with carbon tetrachloride; removing the solvents from said diluted mixture in vacuo to leave a tripeptide trifluoroacetate as a colorless syrup; drying said colorless syrup under vacuum for 24 hours; dissolving said dried syrup in dry dimethylformamide to form a tripeptide trifluoroacetate/dimethylformamide solution; adding N-t-Boc-(gly)Thz to said tripeptide trifluoroacetate/dimethylformamide solution; cooling said solution to 0° C.; adding triethylamine and DEPC to said cooled solution; holding said solution at 0° C. for one hour; warming said cool solution to room temperature for six hours; removing the solvents from said warmed solution in vacuo to provide a residue of protected tetrapeptide N-t-Boc-(gly)Thz-(gly)Thz-L-Val-L-Pro-OMe; dissolving said protected tetrapeptide in trifluoroacetic acid at 0° C.; warming said solution to room temperature; diluting said solution with carbon tetrachloride; removing said solvents in vacuo to leave a tetrapeptide trifluoroacetate as a residue; drying said residue under vacuum for 24 hours; dissolving said dried residue in dimethylformamide to form a dimethylformamide solution; adding N-t-Boc-L-Leu to said dimethylformamide solution; cooling the resulting solution to 0° C.; adding triethylamine and DEPC to said cooled solution; holding said cooled solution at 0° C. for one hour; warming said cooled solution to room temperature for four hours; removing the solvents from said room temperature solution in vacuo to leave a residue; purifying said residue on a silica column in 7% methanol and ethyl acetate to produce a protected pentapeptide N-t-Boc-L-Leu-L-(gln)Thz-(gly)Thz-L-Val-L-Pro-OMe; placing the protected pentapeptide in dioxane and water; treating the dioxane/water solution with sodium hydroxide at room temperature for three hours; diluting the treated solution with diethyl ether to form a diluted treated solution having an aqueous phase; collecting the aqueous phase of said diluted treated solution; adjusting the pH of said aqueous phase to 2 with all cold 2N HCl; extracting said pH adjusted aqueous phase with chloroform to create a plurality of extracts; combining said extracts; drying said combined extracts with anhydrous sodium sulfate; removing the solvent from said dried extracts in vacuo leaving an N-Boc-pentapeptide; precipitating N-Boc-pentapeptide from ethanol with diethyl ether; placing the N-Boc-pentapeptide precipitate in dry dimethoxyethane and dimethylformamide to form a solution; treating said solution with pentafluorophenol and N,N¹-dicyclohexylcarbodiimide at −20° C. in a nitrogen atmosphere; warming said treated solution to room temperature; holding said warmed solution at room temperature for 12 hours; filtering said warmed solution to remove dicyclohexylurea therefrom; removing the solvents from said filtered warmed solution in vacuo to leave a pentapeptide pentafluorophenyl ester; treating said pentapeptide pentafluorophenyl ester with trifluoroacetic acid at room temperature to form a reaction mixture; diluting said reaction mixture with carbon tetrachloride; removing the solvents from said diluted reaction mixture in vacuo to leave a pentapeptide trifluoroacetate ester as the residue; drying said residue under vacuum; dissolving said dried residue in dioxane to produce a solution of 4-pyrrolidinopyridine in t-butanol and dioxane at 95° C.; filtering said solution through celite to create a residue; and removing the solvent from said residue in vacuo to produce Cyclo-[L-Val-L-Pro-L-Leu-L(gln)Thz-(gly)Thz] as an amorphous white powder.

2. A process for synthesizing dolastatin 3 having the structure cyclo, according to claim 1, comprising the first step of adding triethylamine and diethyl phosphorocyanidate to S-proline methyl ester and N-t-Boc-L-valine in 1,2-dimethoxy at 0° C. to form a dipeptide.

3. A process for synthesizing a dolastatin 3 according to claim 2, including the further steps of holding said dipeptide at 0° C. for one hour, allowing the dipeptide to warm to room temperature over 4 hours, and thereafter diluting the warmed dipeptide with ethyl acetate to form a diluted mixture.

4. A process for synthesizing a dolastatin 3 according to claim 3, including the further steps of washing said diluted mixture with 5% HCl followed by sodium hydrogen carbonate followed with saturated brine and removing the solvent therefrom in vacuo to provide N-t-Boc-L-Val-L-Pro-OMe as a colorless syrup.

5. A process for synthesizing a dolastatin 3 according to claim 4, including the further steps of stirring said colorless syrup into a solution of dry dichloromethane at 0° C. and addition trifluoroacetic acid thereto and holding said syrup mixture at 0° C. for one hour.

6. A process for synthesizing a dolastatin 3 according to claim 5, including the further steps of raising said cold syrup-mixture to room temperature, holding said syrup-mixture at room temperature for one hour; diluting the warmed syrup mixture with dry carbon tetrachloride; removing the solvents from said last formed mixtures in vacuo to provide a colorless syrup residue.

7. A process for synthesizing a dolastatin 3 according to claim 6, including the further step of drying said colorless syrup residue under vacuum for twelve hours to leave a dipeptide trifluoroacetate.

8. A process for synthesizing a dolastatin 3 according to claim 7, including the further steps of mixing said dipeptide trifluoroacetate and N-t-Boc-(gly)Thz in dry dimethoxyethane to form a solution, and cooling the solution to 0° C.

9. A process for synthesizing a dolastatin 3 according to claim 8, including the further steps of adding triethylamine and DEPC to the solution; holding the solution 0° C. for one hour; and thereafter warming the solution to room temperature over four hours to form a warmed solution.

10. A process for synthesizing a dolastatin 3 according to claim 9, including the further step of diluting said warmed solution with ethyl acetate, washing said diluted warmed solution with 5% HCl and sodium hydrogen carbonate, and thereafter further washing the washed diluted warmed solution with saturated brine.

11. A process for synthesizing a dolastatin 3 according to claim 10 including the further steps of drying said further washed solution with sodium sulfate and removing the solvent therefrom in vacuo to provide a residue of N-t-Boc-(gly)Thz-L-Val-L-Pro-OMe as a colorless syrup.

12. A process for synthesizing a dolastatin 3 according to claim 11 including the further steps of placing said residue of N-t-Boc-(gly)Thz-L-Val-L-Pro-OMe in dry dichloromethane at 0° C., adding trifluoroacetic acid thereto to form a mixture and holding said mixture at 0° C. for one hour.

13. A process for synthesizing a dolastatin 3 according to claim 12, including the further steps of warming said last formed mixture to room temperature for one hour, diluting the room temperature mixture with carbon tetrachloride, removing the solvents from the diluted mixture in vacuo to leave the tripeptide trifluoroacetate as a colorless syrup, drying the colorless syrup under vacuum for 24 hours, and dissolving the dried syrup in dry dimethylformamide to form a solution.

14. A process for synthesizing a dolastatin 3 according to claim 13 including the further steps of adding N-t-Boc-L-(gln)Thz to the tripeptide trifluoroacetate/dimethylformamide solution, cooling the solution to 0° C. adding triethylamine and DEPC to the cooled solution, holding said solution at 0° C. for one hour, warming the cool solution to room temperature for six hours, and removing the solvents from said warmed solution in vacuo leaving as the residue the protected tetrapeptide N-t-Boc-L-(gln)Thz-(gly)Thz-L-Val-L-Pro-OMe.

15. A process for synthesizing a dolastatin 3 according to claim 14 including the further steps of dissolving said protected tetrapeptide in trifluoroacetic acid at 0° C., warming said solution to room temperature, diluting said solution with carbon tetrachloride, removing said solvents in vacuo to leave a tetrapeptide trifluoroacetate as a residue, drying said residue under vacuum for 24 hours, and dissolving the dried residue in dimethylformamide to form a solution.

16. A process for synthesizing a dolastatin 3 according to claim 15 including the further steps of adding N-t-Boc-L-Leu to said last formed solution, cooling the resulting solution to 0° C., adding triethylamine and DEPC to said cooled solution, holding said cooled solution at 0° C. for one hour; warming said cooled solution to room temperature for four hours; removing the solvents from said room temperature solution in vacuo to leave residue; purifying said residue on a silica column in 7% methanel and ethyl acetate to produce the protected pentapeptide N-t-Boc-L-Leu-L-(gln)Thz-(gly)Thz-L-Val-L-Pro-OMe.

17. A process for synthesizing a dolastatin 3 according to claim 16, including the further steps of placing the protected pentapeptide in dioxane and water, treating the solution formed with sodium hydroxide at room temperature for three hours, and diluting the treated solution with diethyl ether.

18. A process for synthesizing a dolastatin 3 according to a claim 17, further steps of collecting including the aqueous phase of the diluted treated solution adjusting the pH of said aqueous phase to 2 with all cold 2N HCl, extracting said pH adjusted aqueous phase with chloroform to create a plurality of extracts; combining said extract, drying said combined extracts with anhydrous sodium sulfate; removing the solvent from said dried extracts in vacuo leaving the N-Boc-pentapeptide; and precipitating the N-Boc-pentapeptide from ethanol with diethyl ether.

19. A process for synthesizing a dolastatin 3 according to claim 18, including the further steps of placing the N-Boc-pentapeptide precipitate in dry dimethoxyethane and dimethylformamide to form a solution, treating said solution with pentafluorophenol and N.N$^1$-dicyclohexylcarbodiimide at −20° C. in a nitrogen atmosphere; warming said treated solution to room temperature, holding said warming solution at room temperature for 12 hours; filtering said warmed solution to remove dicyclohexylurea therefrom; removing the solvents from said filtered warmed solution in vacuo to leave a pentapeptide pentafluorophenyl ester; and treating said ester with trifluoroacetic acid at room temperature to form a reaction mixture.

20. A process for synthesizing a dolastatin 3 according to claim 19, including the further steps of diluting said reaction mixture with carbon tetrachloride; removing the solvents from said diluted reaction mixture in vacuo to leave pentapeptide trifluoroacetate ester as the residue; drying said residue under vacuum, dissolving said dried residue in dioxane to produce a solution of 4-pyrrolidinopyridine in t-butanol and dioxane at 95° C.; holding said solution and filtering said solution through celite to create a residue.

21. A process for synthesizing a dolastatin 3 according to claim 20 including the further steps of removing the solvent from said residue in vacuo to leave as an amorphous white powder Cyclo-[L-Val-L-Pro-L-Leu-L(gln)Thz-(gln)Thz].

* * * * *